United States Patent [19]
Kane

[11] 3,974,834
[45] Aug. 17, 1976

[54] BODY-IMPLANTABLE LEAD

[75] Inventor: Lawrence M. Kane, Rosenville, Minn.

[73] Assignee: Medtronic, Inc., Minneapolis, Minn.

[22] Filed: Apr. 23, 1975

[21] Appl. No.: 570,917

[52] U.S. Cl. .......................... 128/418; 128/419 P
[51] Int. Cl.² ................................................ A61N 1/04
[58] Field of Search ............... 128/418, 419 P, 404, 128/407–408

[56] References Cited
UNITED STATES PATENTS

| | | | |
|---|---|---|---|
| 2,831,174 | 4/1958 | Hilmo | 128/418 X |
| 3,348,548 | 10/1967 | Chardack | 128/418 |
| 3,416,534 | 12/1968 | Quinn | 128/418 |
| 3,750,650 | 8/1973 | Ruttgers | 128/418 |
| 3,844,292 | 10/1974 | Bolduc | 128/418 |

FOREIGN PATENTS OR APPLICATIONS

| 284,244 | 1/1971 | U.S.S.R. | 128/418 |
|---|---|---|---|

OTHER PUBLICATIONS

Porstmann et al, "P Wave . . . Thoracotomy", Am. J. of Cardiology, vol. 30, July, 1972, pp. 74–76.

*Primary Examiner*—Robert W. Michell
*Assistant Examiner*—Lee S. Cohen

[57] ABSTRACT

A body-implantable, intravascular lead affixed with a pin or pins at its proximal end adapted to be connected to pulse generator and with an electrode or electrodes at its distal end adapted to be securely and permanently attached to a body organ through endothelial tissue. An electrode in the form of a rigid, electrically conductive helix with a sharp tip at the distal end of the lead is adapted to be screwed through endothelial tissue into the body organ. To allow the insertion and guidance of the lead through a body vessel without snagging the body vessel, the lead carries a sleeve shrouding the helix during introduction of the lead that retracts as the corkscrew electrode is screwed into the organ and re-expands to cover the helix in the event that the helix is unscrewed and withdrawn.

10 Claims, 2 Drawing Figures

BODY-IMPLANTABLE LEAD

BACKGROUND OF THE INVENTION

This invention relates to a lead bearing an electrode for connecting a living organ to an electrical device. Notwithstanding its various uses, this invention will be described as an endocardial pacing and sensing lead for connecting a pacemaker to cardiac tissue.

There are generally two types of body-implantable leads—one which requires surgery to expose that portion of the body to which the electrode is to be affixed and the other which is inserted in and guided to the desired location through a body vessel such as a vein. In the cardiovascular field, in particular, there are myocardial and endocardial type leads. Use of a standard myocardial lead such as that disclosed in U.S. Pat. No. 3,216,424, generally provides an excellent electrical contact but requires a thoracotomy in order to affix the electrodes in the outer wall of the heart. This type of surgery is quite strenuous on the patient, particularly an elderly one. Even the improved myocardial leads, e.g., the type disclosed in U.S. Pat. Nos. 3,416,534, 3,472,234 and 3,737,579, require a minor transthoracic surgery to obtain access to the myocardium in order to screw the electrode in place in heart tissue with a special tool or surgical instrument.

Use of a standard endocardial lead of the type shown in U.S. Pat. No. 3,348,548, for example, does not involve serious surgery since the lead is inserted in and guided through a selected vein. However, endocardial leads currently in use are difficult to place and to maintain in proper position and do not insure the best electrical contact since the electrode merely rests against the inner wall of the heart or endocardium at or near the apex of the right ventricle. As a result, the electrodes of such prior art leads tend to become dislodged from their proper position, often resulting in loss of heart capture and thus loss of stimulation of the patient's heart. Also, since the electrodes of an endocardial lead are not secured in the cardiac tissue, the lead tends to move with each contraction of the heart muscle, thereby forming an undesirable callous or fibrotic growth on the inner wall of the right ventricle. Another problem is that with the contraction of the heart, the tip or distal electrode may occasionally puncture the heart wall, resulting in serious injury to the heart and a loss of heart capture.

Many attempts have been made to develop an endocardial lead that can be simply and reliably secured for chronic pacing through endocardial tissue. Typical of such lead designs are those disclosed in U.S. Pat. Nos. 3,754,555 and 3,814,104 which involve a mechanism carried within the lead for advancing prongs or hooks from recesses in the distal end of the lead into endocardial tissue after the lead has been transvenously advanced and positioned within the heart. A further variation on this approach involves the use of a hollow sleeve or introducer catheter of the same length as the lead to shroud the electrode while it is advanced transvenously into the desired position in the heart, whereupon the electrode is advanced from the sleeve or catheter introducer into endocardial tissue. Typical of these latter designs are those disclosed in U.S. Pat. No. 3,844,292 and in the article entitled "New Pacemaker Electrodes" by Max Schaldock appearing in Vol. 17 Transactions: American Society for Artificial Internal Organs, 1971, pp. 29–35.

These prior art endocardial lead designs have not been completely successful in achieving the objects of reliable chronic securement in the endocardial tissue. The prongs or hooks of the former type at times fail to remain in place, or become caught in trabecular cardiac tissue and the electrode remains displaced from and in poor electrical contact with the endocardium. The catheters or sleeves of the latter type add undesirable bulk to the lead as it is advanced through the vein and its increased stiffness makes positioning the electrode tip in the desired location in the heart difficult. In both instances, the complexity of such leads reduces their statistical reliability while raising their cost. If the implanting surgeon should erroneously advance the prongs or hooks from their recesses in the electrode tips or if the same occurs through a malfunction of the lead during advancement of the lead through the veins and heart valves, serious injury could occur as the prongs or hooks snag the valves or the tissue lining the veins.

The body-implantable lead of the present invention combines all the advantages of both the myocardial and endocardial leads with none of the attendant disadvantages of each of these leads as currently found in the prior art. One of the features of the present invention is the provision of a body-implantable intravascular lead which can be lodged in and permanently secured to or removed from the body tissue which it is desired to stimulate, without the use of complex electrode advancement mechanisms or bulky sleeves or catheter introducers. Another feature of the invention is that the body of the lead exclusive of the novel electrode comprises a reliable design that enjoys demonstrated reliability in chronic use and is easily placed in the heart according to well known and proven techniques.

SUMMARY OF THE INVENTION

The above features and advantages of the present invention, as well as others, are accomplished by providing a body-implantable, intravascular lead comprising electrically conductive lead means adapted to be connected at one end to a source of electrical energy and electrode means affixed to the opposite end of the lead means and adapted to be firmly lodged in and permanently secured to or removed from tissue inside the body at a desired location. The lead means and the portion of the electrode means affixed to the lead means are sealed from living animal body fluids and tissue by a material substantially inert to body fluids and tissue. Sleeve means are provided for permitting the lead means and electrode means to be inserted into and guided through a body vessel to a desired location and position inside the body without causing injury to the body vessel and for permitting the electrode means to be firmly lodged in and permanently secured to body tissue at the desired location through the retraction of the sleeve means.

Preferably, the electrode means comprises a rigid helix or corkscrew of a suitable electrode material, and the sleeve means comprises a tube of suitable resilient material affixed to the distal end of the lead means and surrounding and extending beyond the tip of the helix, the tube having a plurality of circumferential pleats which enable it to collapse upon itself as the electrode is screwed into body tissue. Other features, advantages and objects of the present invention will hereinafter become more fully apparent from the following description of the drawings, which illustrate a preferred embodiment.

DESCRIPTION OF THE PREFERRED EMBODIMENT

Figure 1:
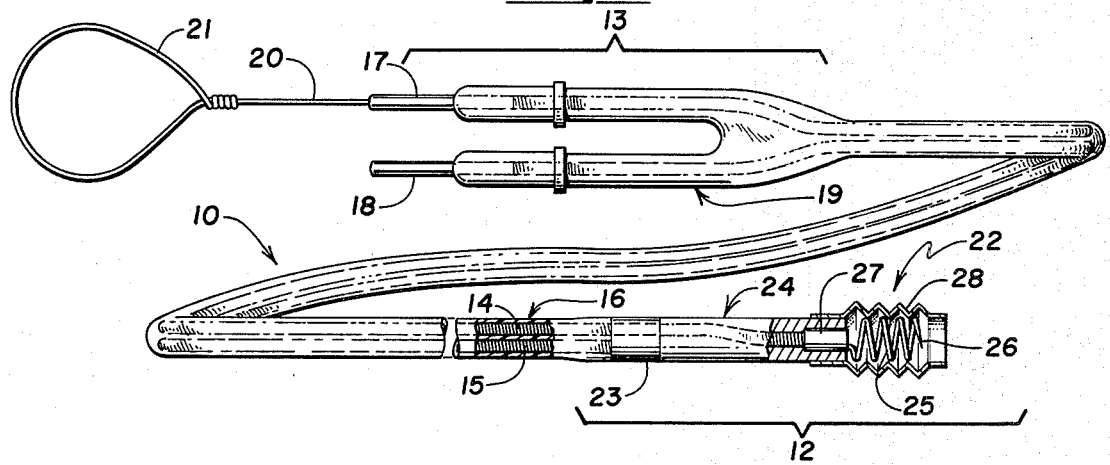
FIG. 1 shows a view of a preferred embodiment of the body-implantable, intravascular lead of the present invention including in part an inside elevation partly in longitudinal section of the electrode end portion of the lead.

Referring now to the preferred embodiment of the invention depicted in FIG. 1, there is shown an intravascular endocardial lead comprising an elongated lead portion 10, a distal electrode end portion 12 and a proximal terminal end portion 13. The lead, in bipolar configuration, comprises a pair of closely wound, coiled conductors 14, 15 each in the form of a spring spirally wound about and along the axis of the conductor. The spring coils 14, 15 extend through the length of the lead 10 in separate lumens of a jacket or sleeve 16 of electrically insulating material.

Each spiral conductor 14, 15 is formed of electrically conductive material offering low electrical resistance and also resistant to corrosion by body fluids. A platinum-iridium alloy is an example of a suitable material. Sleeve 16 is formed of an electrically insulating material, and preferably a silicone rubber such as clean room grade Silastic available from Dow Corning Corporation. This material is additionally suitable because it is inert and well tolerated by body tissue.

At the proximal end 13 of the lead 10, the conductors 14 and 15 are received in and crimped to tubular terminal pins 17 and 18, respectively. A bifurcated boot 19 of the same material as jacket 16 is molded about the terminal pins 17, 18 and the terminal ends of coils 14 and 15 and jacket 16, with the pins 17 and 18 projecting therebeyond. These pins are adapted for insertion in receptacles provided on the pulse generator, which can comprise any suitable implantable pulse generator such as that shown for example in U.S. Pat. No. 3,057,356.

Each of the pins 17, 18 and the respective spiral conductors 14 and 15 is hollow and is thereby adapted to receive a stiffening stylet 20 that extends through the length of the lead 10. The stylet 20 stiffens the lead 10. Its distal end, at the distal end 12 of the lead 10, is bent slightly, while its proximal end, adjacent the proximal end 6 of the lead, is formed to provide means, such as the loop 21, for rotating the stylet about its axis to thereby direct the distal end 12 of the lead as it is inserted through the vein. The stylet imparts rigidity to the proximal portion of the leads and can be manipulated to introduce the appropriate curvature to the distal, electrode end portion facilitating the insertion of the lead into and through a vein, for example one of the jugular veins, to advance the distal end 12 of the lead into the right ventricle of the heart.

At the distal end of the lead 10, a pair of electrodes 22 and 23 are welded or otherwise electrically connected to the ends of the conductors 14 and 15, respectively. The electrode 23 preferably takes the form of a ring of corrosive resistent, electrically conductive material, e.g., platinum or a platinum alloy, a metal oxide or a carbon compound. The ring electrode 23 encircles both coiled conductors 14 and 15. Electrode 22 is similarly electrically connected to the distal end of coiled conductor 14, and the length of coiled conductor 14 extending between electrodes 22 and 23 is insulated by a jacket 24 of the same material as the sleeve 16 molded thereto. In this way, the entire lead is electrically insulated when it is connected to the pulse generator from the body except at the electrodes 22 and 23.

Figure 2:
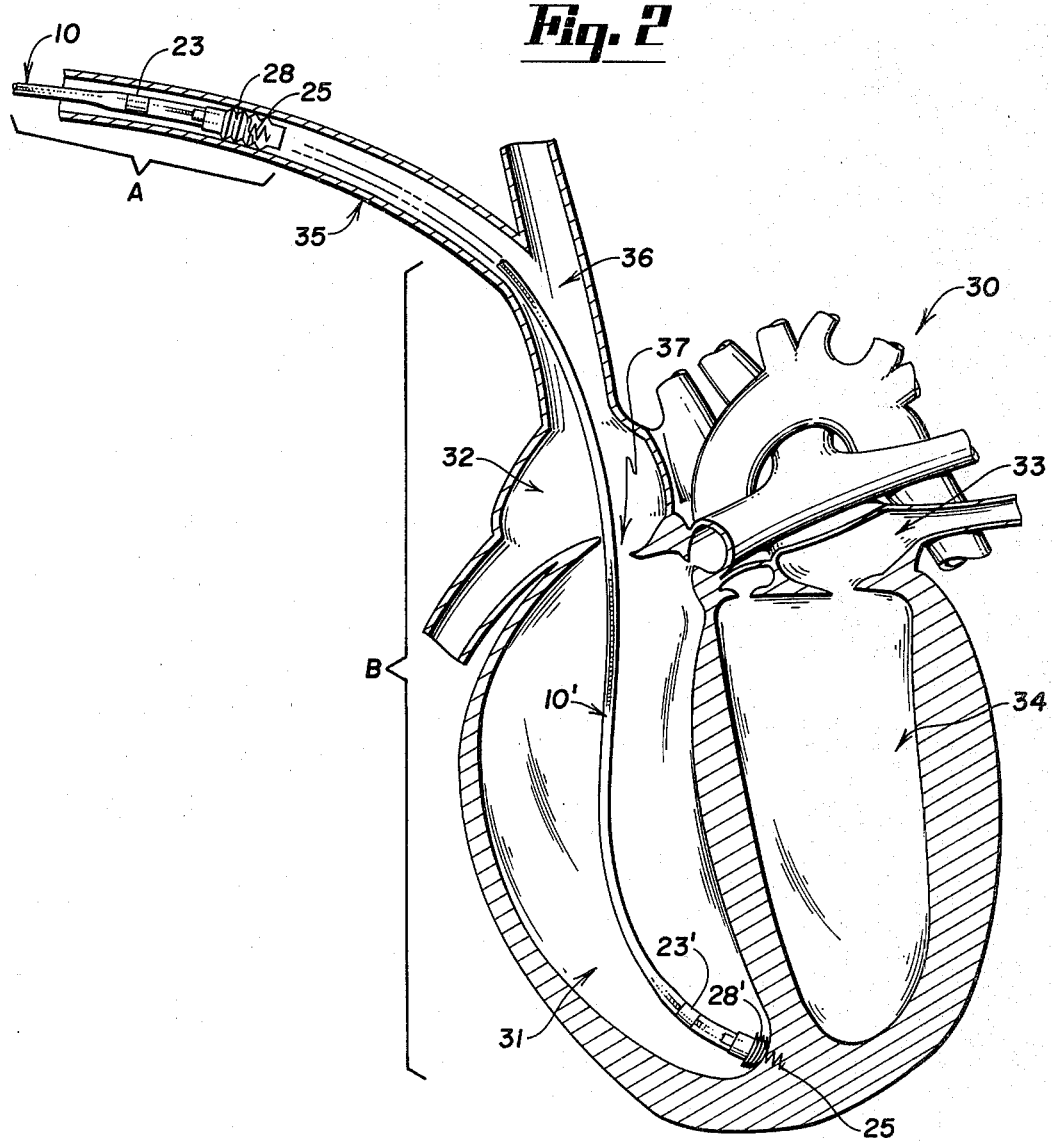
FIG. 2 shows the lead of FIG. 1 being lodged in and permanently secured to the tissue forming the apex of the right ventricle of the heart.

The lead 10 of FIGS. 1 and 2 as described hereintofore corresponds to that disclosed in U.S. Pat. No. 3,348,548. The lead 10 thus far described has been shown to be capable of withstanding constant, rapidly repeated flexing over a period of time which can be measured in years. The conductor coils are wound relatively tightly, although there can be a slight space between adjacent turns. This closely coiled construction provides a maximum number of conductor turns per unit length, thereby providing optimum strain distribution. The spirally coiled spring construction of the conductors also permits a substantial degree of elongation, within the elastic limits of the material, as well as distribution along the conductor of flexing stresses which otherwise might be concentrated at a particular point. Both the conductors 14 and 15, and the insulating bodies 16, 19 and 24 are elastic, and this, together with the coiled construction of the conductors, assures maximum distribution of flexing strains.

Turning now to the improvement of the present invention, it comprises the electrode 22 which further comprises tissue piercing and retaining means and an integral introducer sleeve means for protecting intravascular body vessels from damage by the tissue piercing means during insertion and guidance of the lead that on its own accord retracts from the tissue piercing and retaining means as the same are advanced into and/or through endothelial tissue. More specifically, the electrically conductive electrode 22 is formed in the practice of this invention in the shape of a circular corkscrew or helix 25 having about 5 turns extending about ¼ inch in length and having a nominal outside diameter approximating that of the insulated body of the lead 10, e.g., about 3.2 mm. The corkscrew 25 may be insulated by a thin nonconductive material except for its tip or one or more turns or a portion thereof, so that stimulation current density may be increased in proportion to the conductive electrode area. The helix 25 is welded or otherwise electrically connected to a terminal junction 27 of the conductor 14. Preferably, the helix 25 has a sharpened tip 26 for piercing endocardial tissue and a sufficient number of turns so that as the lead 10 and electrode 22 is rotated by rotation of the proximal terminal end portion 13, the helix 25 may advance through the endocardial tissue into myocardial tissue and be retained therein and inhibited from dislodgement therefrom by the turns of the helix 25.

An introducer sleeve or shroud 28 is fitted over the turns and tip 26 of the helix 25 and sealed to the jacket 24 about the junction 27. The introducer sleeve 28 is made entirely of a silicone rubber compound or other suitable material in a configuration of a thin-walled, accordian-like pleated tube having a number of pleats at least equal to and accommodating the turns of the corkscrew electrode 25. When relaxed, as shown in FIG. 1, the pleats are extended and form 90° angles with respect to one another. The sleeve 28 in its relaxed state is about 0.3 inches in length, has an outside maximum pleat diameter of about 0.16 inches and a wall thickness of about 0.01 inches.

The introducer sleeve 28 is designed to afford protection to the body vessel or vein through which the lead is introduced and to the endothelial tissue of a body organ until the desired implantation position is reached. In the cardiac pacemaker application, once the lead is in the ventricle and is ready to be secured in the desired position of the endocardium, the accordian-like pleats of the sleeve 28 will collapse and fold back over the turns of the helix 25 as it is screwed into the endocardium.

Turning now to FIG. 2, there is shown an illustration of the partially introduced lead 10 of the present invention in a vein (position A) and the completed introduction and permanent securement of the electrode 23 in the tissue forming the apex of the right ventricle of a heart (position B).

In FIG. 2, the heart 30 in cross-section comprises the four chambers, namely, the right ventricle 31, the right atrium 32, the left atrium 33 and the left ventricle 34. In the placement of an endocardial lead, it is preferable to use a venous approach on the low pressure side of the heart, that is, through a vein, e.g., the right or left external jugular veins or the right or left cephalic veins 35, the superior vena cava 36, the right atrium 32, the tricuspid valve 37 and the right ventricle 31. During introduction of the lead 10, it must travel a convoluted course through the veins and must pass through the valve 37 without causing any damage to the tissue. It is also desirable that the lead 10 have a small cross-section so that it will easily pass through the veins without causing excessive stretching of the veins.

In position A of FIG. 2, the distal end 12 of the lead 10 is shown in part. As it is advanced, the sharp tip of the helix 25 is shrouded by the sleeve 28, so that it cannot snag the lining of the veins and the valve 37. Likewise, if the lead 10 is withdrawn, the tip of the electrode 25 is still shrouded and will not injure the intravascular tissue.

In position B, the lead 10' is illustrated screwed into the endocardium at the apex of the right ventricle 31. The corkscrew electrode 25' is fully screwed in by rotation of the entire lead by manipulation of the proximal end 13 (not shown in FIG. 2) of the lead 10'. As it is pressed against the endocardium during the rotation of the lead 10', the sleeve 28' progressively collapses back in its pleats, and the turns of the helix 25' slip past the open end of the sleeve 28' and turn into the cardiac tissue.

In clinically testing the operation of the lead 10 of the present invention, it has been found that the corkscrew or helix 25 can be easily and repeatedly introduced through the vein, through the valve and screwed into the endocardium, unscrewed and withdrawn from the body through the same path without causing any significant damage to the tissue that the lead contacts. As the lead is unscrewed, the pleats of the sleeve 28 expand and the sleeve slips back over the turns of the corkscrew electrode 22. The ease of using the lead of the present invention and the positive securement afforded by a corkscrew or helical electrode design make it readily superior to any of the prior endocardial lead designs.

Although a bipolar lead design has been illustrated in the description of the preferred embodiment, it will be understood that unipolar leads (that is a lead carrying but one electrode and conductor) may as readily employ the novel electrode design of the present invention. Also, it should be understood that other electrode designs or positions along the lead could be substituted for that of the electrode 23. It should be understood that although the use of the lead 10 has been described for use in a cardiac pacing system, lead 10 could as well be applied to other types of body stimulating systems.

It should be further understood, of course, that the foregoing disclosure relates only to the best mode known to the inventor of many possible modes of practicing the invention and that numerous modifications may be made therein without departing from the spirit and scope of the invention as set forth in the appended claims.

What is claimed is:

1. A body-implantable, intravascular lead adapted to be connected at its proximal end to a source of electrical energy and permanently secured at its distal end through the endothelial tissue of a living animal body for electrical stimulation thereof and for detecting electrical signals comprising:

electrically conductive lead means for insertion in and guidance through a body vessel to a desired location and position inside an organ of a living animal body, the lead means having a cross-section which will fit within a body vessel;

electrode means affixed to the distal end of said lead means and adapted to supply electrical impulses to tissue at a desired location inside the living animal body, said electrode means including a tissue piercing portion and further including separate tissue engaging means for allowing said electrode means to be firmly and permanently secured through the endothelial tissue at the desired location;

material means substantially inert to body fluids and tissue encasing said lead means and a portion of said electrode means for sealing them from living animal body fluids and tissue; and sleeve means attached to said distal end of said lead means for shrouding said tissue piercing portion and said tissue engaging means thereby allowing the insertion and guidance through a body vessel of said lead means while preventing injury to said body vessel by said tissue piercing portion and for retracting upon contact with endothelial tissue from said tissue piercing portion and said tissue engaging means for allowing said electrode means to be firmly lodged in and secured through the endothelial tissue.

2. The body-implantable, intravascular lead of claim 1 wherein said sleeve means further comprises:

an elongated tube of a resilient material inert to body fluids and tissue extending from said distal end of said lead means surrounding said electrode means and extending beyond said tissue piercing portion.

3. The body-implantable, intravascular lead of claim 1 wherein said electrode means further comprises:

a rigid helix having a point comprising said tissue piercing portion and a number of turns comprising said tissue engaging means, said helix being adapted to be screwed into endothelial tissue to firmly lodge in and permanently secure said electrode means through the endothelial tissue.

4. The body-implantable, intravascular lead of claim 3 wherein said sleeve means further comprises:

an elongated tube of resilient material inert to body fluids and tissue extending from said distal end of said lead means surrounding said tissue engaging turns of said helix and extending beyond said tissue piercing point, said tube having a number of circumferential pleats adapted to collapse to retract said sleeve means as said helix is screwed into endothelial tissue and further adapted to re-extend as said helix is unscrewed from endothelial tissue.

5. The body-implantable, intravascular lead of claim 4 further comprising:
  means for facilitating the insertion and guidance of said lead means through a body vessel and the screwing of said helix into endothelial tissues.

6. The body-implantable, intravascular lead of claim 3 further comprising:
  means for facilitating the insertion and guidance of said lead means through a body vessel and the screwing of said helix into endothelial tissues.

7. In a body-implantable lead that includes a flexible electrical conductor means having a proximal end thereof adapted for connection to a power supply and wherein the distal end portion of the conductor means comprises an uninsulated, conductive, rigid helix having a number of turns and ending in a point adapted for attachment to body tissue, and means substantially inert to body fluids and tissue enclosing substantially the entire length of said conductor means except for said distal end portion for permitting said lead to be implanted within the body, the improvement which comprises:
  sleeve means attached to said distal end of said conductor means for shrouding said helix and for retracting from said helix upon contact with body tissue as said helix is screwed into body tissue.

8. The body-implantable lead of claim 7 wherein said sleeve means further comprises:
  an elongated tube of resilient material substantially inert to body fluids and tissue extending from said distal end of said conductor means surrounding the turns of said helix and extending beyond its point.

9. The body-implantable lead of claim 8 wherein said tube of said sleeve means further comprises:
  a number of circumferential pleats in said tube adapted to extend said tube beyond the point of said helix during insertion and guidance or withdrawal of said lead through a body vessel and adapted to collapse said tube upon itself as said helix is screwed into body tissue.

10. A body-implantable lead of materials substantially inert to body fluids and tissue having a length of electrically insulated conductor, a connector pin at a proximal end of the conductor, an electrode adapted to contact the tissue of a living animal body at the distal end of the conductor, said electrode including tissue engaging means for securely engaging said electrode in contact with the tissue characterized by:
  sleeve means attached to the distal end of the conductor for shrouding said tissue engaging means to prevent the tissue engaging means from impeding the insertion and guidance through a body vessel of said lead and for retracting upon contact with tissue from said tissue engaging means to allow said tissue engaging means to securely engage said electrode in contact with the tissue.

* * * * *